United States Patent [19]

Lane

[11] 4,443,895
[45] Apr. 24, 1984

[54] LOW-PRESSURE FIXATION OF VALVULAR TISSUE INTENDED FOR IMPLANTATION

[75] Inventor: Ernest Lane, Huntington Beach, Calif.

[73] Assignee: American Hospital Supply Corporation, Irvine, Calif.

[21] Appl. No.: 396,629

[22] Filed: Jul. 9, 1982

Related U.S. Application Data

[62] Division of Ser. No. 275,749, Jun. 22, 1981, Pat. No. 4,372,743.

[51] Int. Cl.³ .......................... A61F 1/04; C14B 1/26
[52] U.S. Cl. .......................................... 3/1.5; 425/2; 69/19
[58] Field of Search .................... 425/2; 604/106, 264, 604/268; 69/19, 19.1; 8/94.11; 3/1, 1.4, 1.5

[56] References Cited

U.S. PATENT DOCUMENTS

| | | | |
|---|---|---|---|
| 3,620,218 | 11/1971 | Schmitt | 3/1.4 |
| 3,655,306 | 4/1972 | Ross et al. | 3/1.5 |
| 3,966,401 | 6/1976 | Hancock et al. | 3/1.5 |
| 4,050,893 | 9/1977 | Hancock et al. | 3/1.5 |
| 4,247,292 | 1/1981 | Angeu | 3/1.5 |
| 4,345,340 | 8/1982 | Rosen | 3/1.5 |
| 4,350,492 | 9/1982 | Wright et al. | 3/1.5 |

Primary Examiner—Richard J. Apley
Assistant Examiner—David J. Isabella
Attorney, Agent, or Firm—Gordon L. Peterson

[57] ABSTRACT

A method of obtaining fixation of an animal aortic valve intended for implantation, including subjecting the aortic valve to a tanning fluid at a differential pressure across the valve leaflets in a direction to urge the valve leaflets closed and with the tanning fluid tending to distort the aortic valve. The differential pressure across the valve leaflets is greater than zero and less than about four mm Hg. An insert restrains the valve against substantial distortion during the time the valve is subjected to the tanning fluid.

5 Claims, 6 Drawing Figures

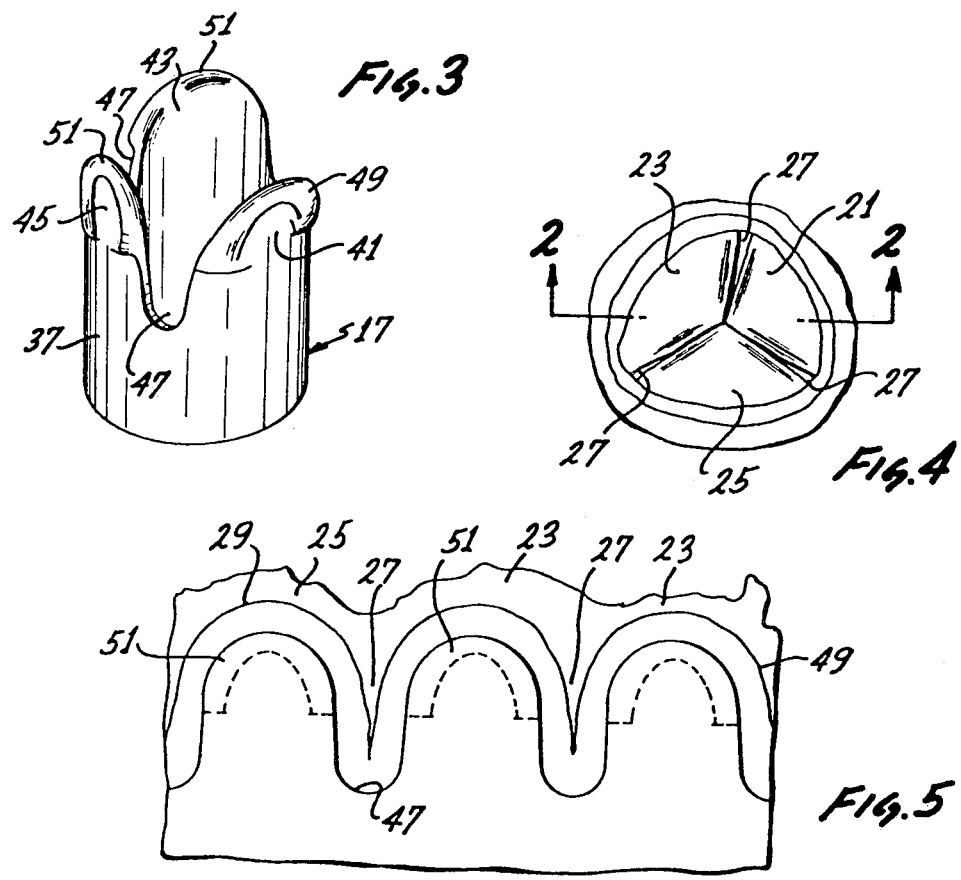
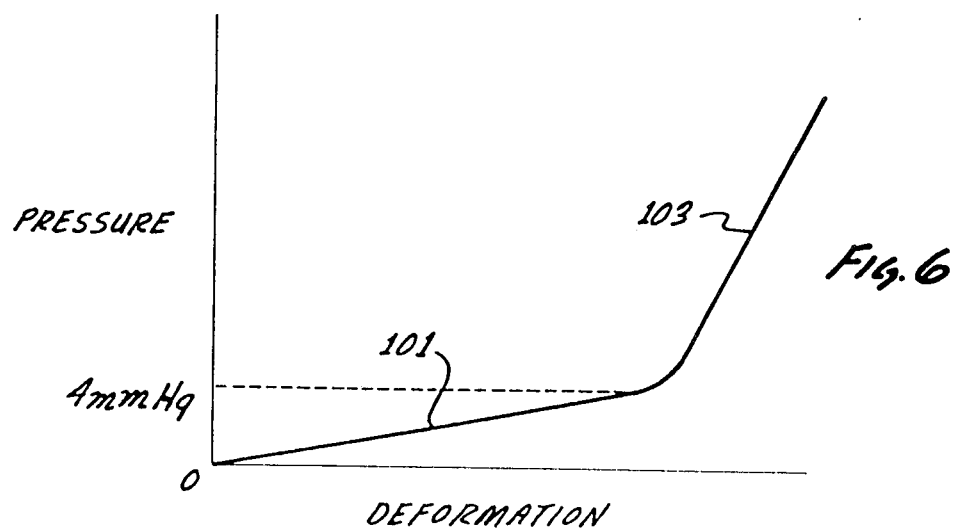

LOW-PRESSURE FIXATION OF VALVULAR TISSUE INTENDED FOR IMPLANTATION

This application is a division of the application Ser. No. 275,749 filed June 22, 1981 now U.S. Pat. No. 4,372,743.

BACKGROUND OF THE INVENTION

Animal heart valves, such as porcine heart valves, have been used for implantation in humans. To prepare the animal heart valve for implantation, it is common practice to tan the valve. Tanning renders the animal tissue relatively inert with respect to the living host environment and brings about fixation of the tissue, i.e., stabilization of the tissue so that it has a fixed configuration.

As disclosed in Hancock et al U.S. Pat. Nos. 3,966,401 and 4,050,893 and Angell et al U.S. Pat. No. 3,983,581, it is known to tan animal heart valves by utilizing a tanning fluid under pressures which may range from 20 mm Hg to 120 mm Hg. These methods provide a substantial internal pressure on the heart valve. According to Hancock et al U.S. Pat. No. 4,050,893, the use of pressures in the physiologic range, i.e., 80–120 mm Hg causes the tissue to assume substantially its natural configuration during the tanning process and in fixing the valve in its natural contour so that it will retain its shape following the tanning process.

Recent reports by Broom, Neil D., *An In Vitro Study of Mechanical Fatigue in Glutaraldehyde-Treated Porcine Aortic Valve Tissue,* Biomaterials, Volume 1, Jan. 3, 1980, and Broom, Neil D. and Thomson, Fergus J., *Influence of Fixation Conditions on the Performance of Glutaraldehyde-Treated Porcine Aortic Valves: Towards A More Scientific Basis,* Thorax, Volume 34, 1979, describe problems that occur in the structure of the valve leaflets during tanning under pressures at the physiological levels. Briefly, the valve tissue of a porcine aortic valve includes collagen fibers arranged in a waveform or crimped condition. When internal pressures are applied to the valve during the tanning process, the collagen waveform tends to straighten out, and the degree to which the waveform returns to its original condition following removal of the internal pressure is a function of the magnitude of the internal pressure applied during the tanning process. If the collagen does not return to its original waveform condition, the stiffness of the valve leaflet is adversely affected. This has an adverse influence on the manner in which the valve leaflets open, and it provides regions of local strain or kinks in the valve leaflets during opening. It is believed that loss of the waveform geometry also reduces the fatigue durability of the valve leaflets.

According to these publications, obtaining fixation at the higher internal pressure levels results in considerable permanent loss of the collagen waveform so that, upon removal of the relatively high internal pressure, much of the collagen does not return to its original waveform condition. It is further reported by the same authors that a pressure of 100 mm Hg eliminates the waveform geometry entirely and that pressures even as low as 4 mm Hg result in significant reductions in the waveform after removal of the internal pressure.

To avoid these undesirable results, it is suggested in the above-noted publications that the tanning process should be carried out at pressures in the range of slightly above zero to about 4 mm Hg. However, an inherent effect of subjecting the valve to the tanning fluid is that the valve tends to shrink and distort. The relatively low internal pressure of just above zero to about 4 mm Hg is insufficient to retain the animal heart valve against shrinkage and distortion during the tanning process. Accordingly, the valve may become fixed in a configuration which is unsuited for use in an implant.

One prior art method for tanning at essentially zero pressure differential across the valve leaflet is to pack the valve leaflet with a batting, such as a Dacron or cotton batting, to assure that the leaflets contact each other to provide a competent valve. However, great care must be taken in packing the delicate valve leaflets, and even with the exercise of considerable care and diligence in packing, the mechanical stresses exerted on the valve leaflets cannot be measured and are subject to operator variability. In addition, abrasion between the valve leaflets and the batting results in changes in surface morphology, and a substantial amount of time is required to carefully pack the valve leaflets with the batting.

SUMMARY OF THE INVENTION

This invention accomplishes fixation of an animal heart valve by subjecting the valve to a tanning fluid at relatively low pressures to avoid permanent loss of the collagen waveform. During the tanning process, the valve is mechanically restrained to substantially avoid shrinkage and distortion, and packing the valve leaflets is eliminated.

With this invention, an animal aortic heart valve is subjected to a tanning fluid at a differential pressure across the valve leaflets in a direction to urge the valve leaflets closed. The differential pressure should be sufficient to hold the valve leaflets closed, and, therefore, should be greater than zero. On the other hand, the differential pressure should not be so great as to provide a significant percentage of irreversible alterations in the waveform geometry of the collagen of the valve leaflets. For a porcine aortic valve and based upon experimental data presently available, this establishes an upper differential pressure limit of about 4 mm Hg, although particular circumstances and/or additional experimental data may prove that 4 mm Hg is not an absolute upper differential pressure limit.

Because the internal pressure on the valve is insufficient to restrain the valve against distortion during the tanning process, this invention provides for other forms of restraints. Preferably, restraint is accomplished mechanically by inserting an insert into the aortic valve so that the insert is present for restraining purposes during the tanning process. The insert has numerous features which, when appropriately employed, provide a particularly advantageous restraint against the distortion which inherently tends to occur as a result of the tanning process.

To illustrate, an aortic valve may be considered as including a tubular aorta segment and three delicate valve leaflets, each of which is affixed to the aorta segment at a juncture. The insert preferably has a leading end and is inserted into the aorta segment to a location at which the leading end is closely adjacent the junctures. When the valve is subjected to a tanning fluid, it tends to shrink and this tends to draw the valve leaflets inwardly. By inserting the insert to this location, the insert appropriately engages the valve to substantially prevent it from shrinking and distorting. The insert is preferably relatively rigid and it must have sufficient rigidity to enable it to retain the valve against distortion.

It is desirable to avoid contacting the delicate valve leaflets with the insert, and accordingly, the insert preferably engages the valve on the side of the junctures remote from the valve leaflets. Also, the insert may advantageously include three axially extending projections separated circumferentially by recesses. In the installed condition, the three projections engage and restrain the valve adjacent the junctures, respectively, and the recesses confront the commissures to minimize shrinkage and distortion of the aortic tissue at the valve annulus and in the area of the sinuses of Valsalva The aortic valve is not symmetrical. More specifically, the interventricular wall extends to the base of the right coronary valve leaflet making a kind of support for this valve leaflet. The muscular part of this leaflet can be weakened by trimming, but in any event, the right coronary valve leaflet provides a slight asymmetry. To accommodate this, one of the projections has an outer tissue supporting surface adjacent its free end which lies more radially outwardly than the corresponding outer tissue supporting surfaces of the other two projections. This projection, i.e., the one with an outer surface which lies more radially outwardly than the others, is located in the sinus of Valsalva of the right coronary valve leaflet for contact with the wall of the aorta segment. This asymmetry of the insert and its orientation are very important in minimizing shrinkage and distortion near the right coronary valve leaflet. The asymmetry of the insert can be brought about in different ways, such as by different angles of radial outward inclination on the projections, providing segments near the free ends of each of the projections which project radially outwardly different distances, etc.

To avoid damaging the valve, the edges of the insert which contact the tissue are rounded in elevation and in axial cross section. The insert is preferably tubular to enable a tanning fluid to be supplied to the interior of the valve through the insert. The insert can be constructed of any biocompatible material which is inert to the tanning fluid being utilized and is preferably transparent to facilitate visual placement of the insert in the valve.

The invention, together with additional features and advantages thereof, may best be understood by reference to the following description taken in connection with the accompanying illustrative drawings.

BRIEF DESCRIPTION OF THE DRAWINGS

FIG. 3 is a perspective view of the insert.

FIG. 4 is a top plan view of the aortic valve of FIG. 2.

FIG. 5 is a simplified view of the insert and valve of FIG. 2 laid flat to show the zone of contact between the two.

FIG. 6 is a plot of differential pressure across the valve leaflets and collagen strain.

DESCRIPTION OF THE PREFERRED EMBODIMENT

Figure 1:
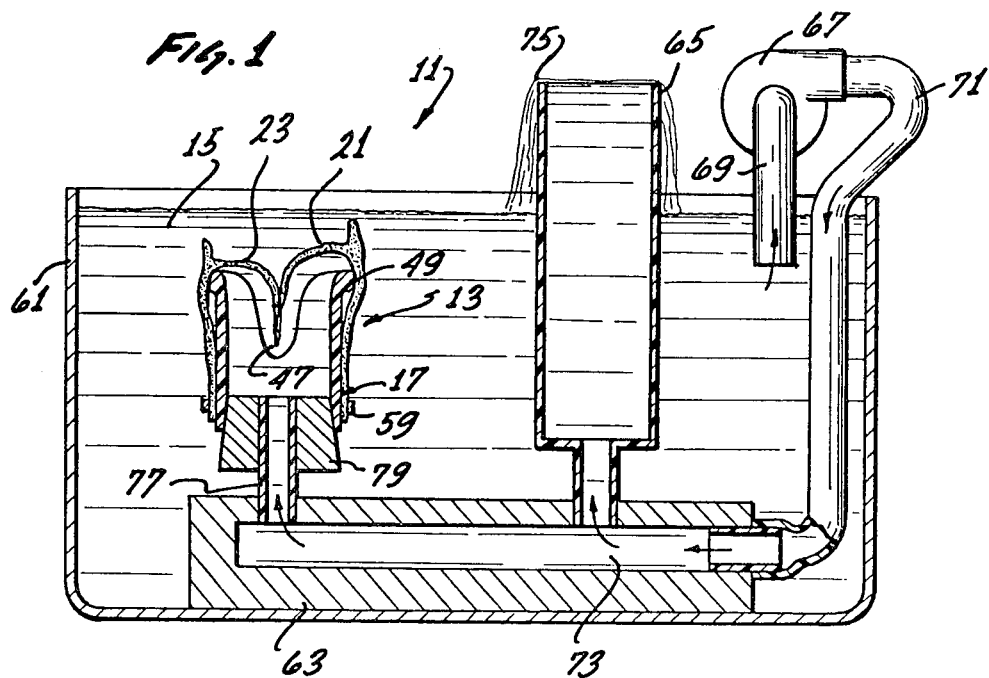
FIG. 1 is a somewhat schematic sectional view illustrating an apparatus for tanning animal aortic valves in accordance with the teachings of this invention.
Figure 2:
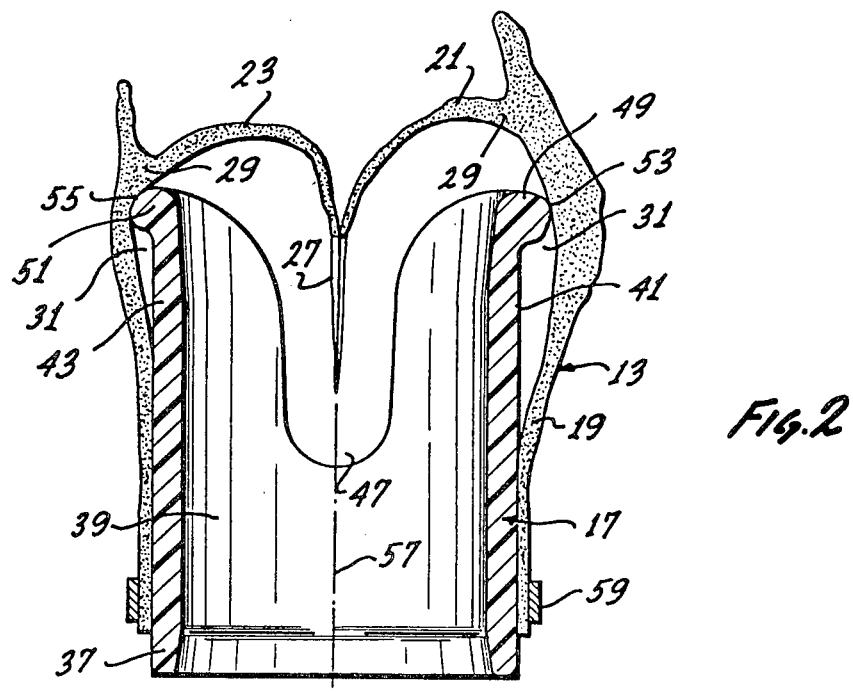
FIG. 2 is a sectional view on line 2—2 of FIG. 4 of one form of insert constructed in accordance with the teachings of this invention inserted into a porcine aortic valve and clamped in position.

FIG. 1 shows an apparatus 11 for obtaining low pressure fixation of a porcine aortic valve 13 utilizing a tanning solution 15 and an insert 17. With reference to FIGS. 2 and 4, the aortic valve 13 has been excised from the heart and it includes a tubular aorta segment which, in the form illustrated, is a portion of the ascending aorta 19 and three valve leaflets 21, 23 and 25. The bulk of the myocardial tissue has been trimmed from the valve 13 to minimize distortion during fixation, and the coronary arteries (not shown) are tied off. Adjacent edges of the valve leaflets 21, 23 and 25 meet to form commissures 27 at the junctions between adjacent valve leaflets. Each of the valve leaflets 21, 23 and 25 may be considered as joined to the ascending aorta 19 along a juncture 29. The wall of the ascending aorta 19 adjacent the junctures 29 forms sinuses 31 of Valsalva. The valve leaflet 21 is the right coronary leaflet.

The insert 17 in the embodiment illustrated is integrally molded from a suitable biocompatible material which is compatible with the tanning solution 15, such as a suitable polyester or acrylic material. The insert 17 is preferably sufficiently transparent so that its position within the aortic valve 13 can be accurately visually observed.

The insert 17 includes a tubular peripheral wall 37 of a generally cylindrical configuration which is open at both ends and which defines a generally axial cylindrical passage 39 extending through the insert. The peripheral wall has three generally axially extending projections 41, 43 and 45, with each adjacent pair of projections being circumferentially spaced by a recess 47. The projection 41 terminates outwardly at its free end in a segment or rib 49, and the projections 43 and 45 similarly terminate at their free ends in ribs 51. As best seen in FIG. 2, the ribs 49 and 51 project radially outwardly to provide outer tissue supporting surfaces 53 and 55, respectively. The recesses 47 prevent contact with, and damage to, the valve leaflets 21, 23 and 25 at the commissures 27. To avoid damaging the tissue which they contact in the valve 13, the ribs 49 and 51 and the free ends of the projections 41, 43 and 45, in the embodiment illustrated, are curved in axial cross section as shown in FIG. 2 and are also curved as viewed in side elevation as shown in FIG. 3.

The recesses 47 are similarly formed by smoothly curved edges on the projections 41, 43 and 45. The leading end portion, i.e., the upper end portion as viewed in FIGS. 2 and 3, is asymmetrical about an axis 57 which is the central axis of the passage 39 and of the insert 17. Specifically, the radial spacing between the outer tissue supporting surface 53 and the axis 57 is greater than the radial spacing between the axis 57 and the outer tissue supporting surfaces 55. The radial spacing between both of the outer tissue supporting surfaces 55 and the axis 57 is the same. In the embodiment illustrated, the projections extend slightly radially outwardly as they extend toward their free ends.

To carry out the tanning process and obtain fixation of the valve 13, the leading end of the insert 17 is inserted into the open end of the ascending aorta 19 to the location shown in FIG. 2. The valve 13 is then suitably affixed to the insert 17 as by sutures (not shown) or a strap 59 which encircles the aorta 19 adjacent its open end and clamps it to the insert. The strap 59 holds the valve 13 against axial movement relative to the insert 17 and should not be placed on any part of the valve which will be used in the implant made from the valve 13.

When in position within the valve 13, the projections 41, 43 and 45 engage, or lie closely adjacent, the junctures 29, respectively, and the recesses 47 confront, and lie radially inwardly of, the commissures 27, respectively, as shown in FIG. 2. The insert 17 does not contact the valve leaflets 21, 23 and 25. The projection 41 is provided for supporting the valve 13 in the region of the right coronary so that the outer tissue supporting surface 53 of the rib 49 engages the aortic wall of the aorta 19 adjacent the right coronary valve leaflet 21. The ribs 49 and 51 engage and support the aortic wall of the aorta in the sinuses of Valsalva 31. Except for the sinuses of Valsalva, the outside diameter of the insert 17 is approximately equal to the inside diameter of the adjacent regions of the ascending aorta 19. The radial spacing between the axis 57 and the outer tissue supporting surfaces 53 and 55 represents the desired position beyond which the adjacent junctures 29 should not be allowed to distort or shrink.

FIG. 5 shows how the projections 41, 43 and 45 thoroughly support the valve 13 without contacting the valve leaflets 21, 23 and 25. As viewed in FIG. 5, the junctures 29 are generally semicircular, and the ribs 49 and 51 engage the aorta 19 just below the junctures. The recesses 47 and the curvature (as seen in FIG. 5) of the projections prevent contact of the insert with the valve leaflets.

The apparatus 11 may be used to tan one or more of the valves 13 which have an insert 17 within them as shown in FIG. 2. The apparatus 11 includes a tank 61, a header 63, a reservoir 65 coupled to the header 63, a pump 67, an intake conduit 69 leading from the tanning solution 15 within the tank to the intake of the pump, and a discharge conduit 71 leading from the discharge of the pump to the header 63. The header 63 is fixed within the tank 61 and has a passage 73 coupled to the conduit 71 and to the lower end of the reservoir 65. The tanning solution 15 fills the tank 61 to a predetermined height, and the reservoir 65 has an open top 75 which lies a prescribed distance above the elevation of the tanning solution 15 in the tank 61. The difference in elevation between the levels of the tanning solution 15 within the tank 61 and the reservoir 65 represents the differential pressure across the valve leaflets 21, 23 and 25 at which the tanning process will be carried out. This is a static head and flow is required only to make up for leakage, and a slight initial flow is required to close the valve leaflets 21, 23 and 25. In the embodiment illustrated, the head represented by the difference in these two elevations is 2 mm Hg.

The passage 73 in the header 63 also communicates with a riser 77 having a stopper 79 mounted on it. The upper end of the stopper 79 is received within the lower end of the insert 17 so that the stopper and insert cooperate to mount the valve 13 vertically within the tank 61. Additional valves 13 may be similarly mounted on the header 63, if desired.

The tanning solution 15 may be of any composition suitable for tanning the porcine aortic valve 13. For example, the tanning solution 15 may be a suitable solution of glutaraldehyde.

With the components in the position of FIG. 1, the pump 67 can be operated to pump tanning solution 15 from the tank 61 through the conduits 69 and 71, the header 63 and over the top 75 of the reservoir 65 as may be required to maintain the desired static head. The flow, if any, is exceedingly small to avoid subjecting the leaflets 21, 23 and 25 to any velocity head. Thus, the interior of the valve 13, including the interior of the valve leaflets 21, 23 and 25, is subject to a static pressure increasing to the height of the top 75. Simultaneously, the outer surfaces of the valve 13 are subjected to the tanning solution 15 at a static pressure corresponding to the elevation of the tanning solution in the tank 61. Thus, the differential pressure to which the aortic valve 13, and in particular, the delicate valve leaflets 21, 23 and 25 is subjected corresponds to the difference in elevation between the top 75 of the reservoir 65 and the elevation of the tanning solution 15 within the tank 61. This assures that the internal pressure within the valve 13 will exceed the exterior pressure so that the valve leaflets 21, 23 and 25 will be urged toward the closed position. Also, because the liquid level in the reservoir 65 cannot rise above the top 75, the maximum internal pressure is also regulated. By utilizing a known volume of the tanning solution 15 in containers of known volume, the differential pressure across the valve leaflets 21, 23 and 25 can be maintained at the desired nominal value.

The action of the tanning solution 15 on the valve 13 tends to shrink and distort the valve. However, the engagement of the valve 13 in the region of the sinuses of Valsalva 31 against the relatively rigid projections 41, 43 and 45 prevents significant distortion of these critical portions of the valve during the tanning process. The tissue adjacent the right coronary valve leaflet 21 contains additional muscle as shown in FIG. 2. The specially configured projection 41 engages the aortic wall adjacent the right coronary leaflet 21 to prevent significant distortion and shrinkage in this region. Also, the lower regions of the valve 13 engage the outer periphery of the insert 17 at and below the projections 41, 43 and 45 to also hold these regions against shrinkage and distortion. The valve 13 is subjected to the action of the tanning solution 15 for a sufficient time to obtain fixation of the valve, and this may take, for example, about eight hours.

FIG. 6 shows the relationship between valve leaflet deformation as a function of differential pressure across the valve leaflet during the tanning process. As the differential pressure rises from zero to about 4 mm Hg, the valve leaflets deform linearly along a segment 101 of the curve. During this time, deformation is relatively substantial due to extension of the waveform of the collagen or uncrimping of the collagen. Generally, the deformation represented by the segment 101 is not harmful because, when the differential pressure is removed, the collagen returns to its original waveform or crimped condition. However, above about 4 mm Hg of differential pressure, the rate of deformation is substantially reduced, and this is graphically indicated by a segment 103 of the curve which has a much steeper slope; thus, indicating a much slower rate of change of deformation with respect to differential pressure. The deformation of the valve leaflets represented by the segment 103 of the curve results in permanently removing, to a degree that increases with pressure, the collagen waveform rather than elastically stretching or uncrimping of the collagen. This destruction of the collagen waveform produces the harmful affects described above. Available experimental data indicates that the separation of the segments 101 and 103 is at about 4 mm Hg differential pressure, although some modest variation in this could reasonably be expected in that tissue is not homogeneous, and thus all heart valves upon which the process is performed would not be expected to have identical structural properties. Also, as new experimental data becomes available, refinements of the upper limit on the differential pressure at which collagen straining becomes unacceptable may become known. Of course, some straining of the collagen may occur at under 4 mm Hg but generally it is believed that collagen strain at differential pressures under 4 mm Hg is not particularly harmful.

Although an exemplary embodiment of the invention has been shown and described, many changes, modifications and substitutions may be made by one having ordinary skill in the art without necessarily departing from the spirit and scope of this invention.

I claim:

1. An insert for use in restraining an animal heart valve against distortion during fixation, said insert comprising:

a tubular peripheral wall open at both ends and defining a generally axial passage;

said peripheral wall having three generally axially extending projections, each of said projections terminating axially outwardly in a curved end surface as viewed in side elevation, each adjacent pair of said projections being circumferentially spaced by a recess;

each of said projections having an outer tissue supporting surface closely adjacent its free end, the outer tissue supporting surface of one of said projections lying more radially outwardly of the axis of said passage than the outer tissue supporting surfaces of the other two projections whereby said outer tissue supporting surfaces are arranged eccentrically about the axis of said passage; and at least the exposed surface of said insert being constructed of a biocompatible material.

2. An insert as defined in claim 1 wherein each of said curved end surfaces is curved as viewed in axial cross section and said outer tissue supporting surfaces lie farther radially outwardly than the peripheral wall adjacent the projections.

3. An insert as defined in claim 1 wherein each of said projections terminates in an end portion which includes a segment projecting radially outwardly, said outer tissue supporting surfaces being on said segments, respectively.

4. An insert as defined in claim 1 wherein the tubular wall is transparent.

5. An insert as defined in claim 3 wherein each of said segments includes a curved rib.

* * * * *